United States Patent [19]

Lustig et al.

[11] Patent Number: 5,145,369
[45] Date of Patent: Sep. 8, 1992

[54] DENTAL TOOL DRIVING APPARATUS HAVING ROTATING AND ROTO-RECIPROCATING MOTIONS

[75] Inventors: L. Paul Lustig, 304 Greenwood St., Newton, Mass. 02159; Andrew Tybinkowski, 39 Burning Bush Rd., Boxford, Mass. 01921

[73] Assignee: L. Paul Lustig, Newton Centre, Mass.

[21] Appl. No.: 512,836

[22] Filed: Apr. 23, 1990

[51] Int. Cl.⁵ .......................... A61C 1/07; A61C 3/03; A61C 3/08
[52] U.S. Cl. .................................. 433/118; 433/122; 433/123
[58] Field of Search .................. 433/118, 123, 122

[56] References Cited

U.S. PATENT DOCUMENTS

| | | | |
|---|---|---|---|
| 462,530 | 11/1901 | Booth . | |
| 735,968 | 8/1903 | Grobe . | |
| 2,968,960 | 1/1961 | Fulop | 74/22 |
| 2,970,483 | 2/1961 | Schrum, Sr. | 74/22 |
| 3,521,497 | 7/1970 | Schmuck | 74/22 |
| 3,602,053 | 8/1971 | Steiner | 433/122 |
| 3,661,018 | 5/1972 | Keefer et al. | 74/22 R |
| 3,969,823 | 7/1976 | Nakanishi | 32/27 |
| 4,084,280 | 4/1978 | May | 15/22 R |
| 4,156,620 | 5/1979 | Clemens | 134/6 |
| 4,173,828 | 11/1979 | Lustig et al. | 433/122 |
| 4,175,324 | 11/1979 | Arai | 433/122 |
| 4,233,850 | 11/1980 | Edwardson | 74/44 |
| 4,289,849 | 9/1981 | Lustig et al. | 433/123 |
| 4,397,055 | 8/1983 | Cuchiara | 15/22 R |
| 4,630,493 | 12/1986 | Kato | 74/22 R |
| 4,781,588 | 11/1988 | Granier | 433/123 |
| 4,834,653 | 5/1989 | Edwardson | 4/118 |

FOREIGN PATENT DOCUMENTS 648487 1/1951 United Kingdom .
2137503 10/1984 United Kingdom .

Primary Examiner—Robert P. Swiatek
Assistant Examiner—Nicholas D. Lucchesi
Attorney, Agent, or Firm—Lahive & Cockfield

[57] ABSTRACT

A manually deployable power tool for dental treatment and other uses drives an output shaft with continuous rotary motion, combined with selected axial reciprocation of adjustable stroke length. The drive mechanism for imparting this combined motion to the output shaft has a single rotary input drive coupled with an adjustable cam mechanism. The cam mechanism produces the reciprocating motion in response to the driven rotation of the output shaft. The tool drive mechanism has a high degree of axial symmetry, and is arranged to facilitate the delivery of liquid material to the output, tool-carrying end of the output shaft.

25 Claims, 9 Drawing Sheets

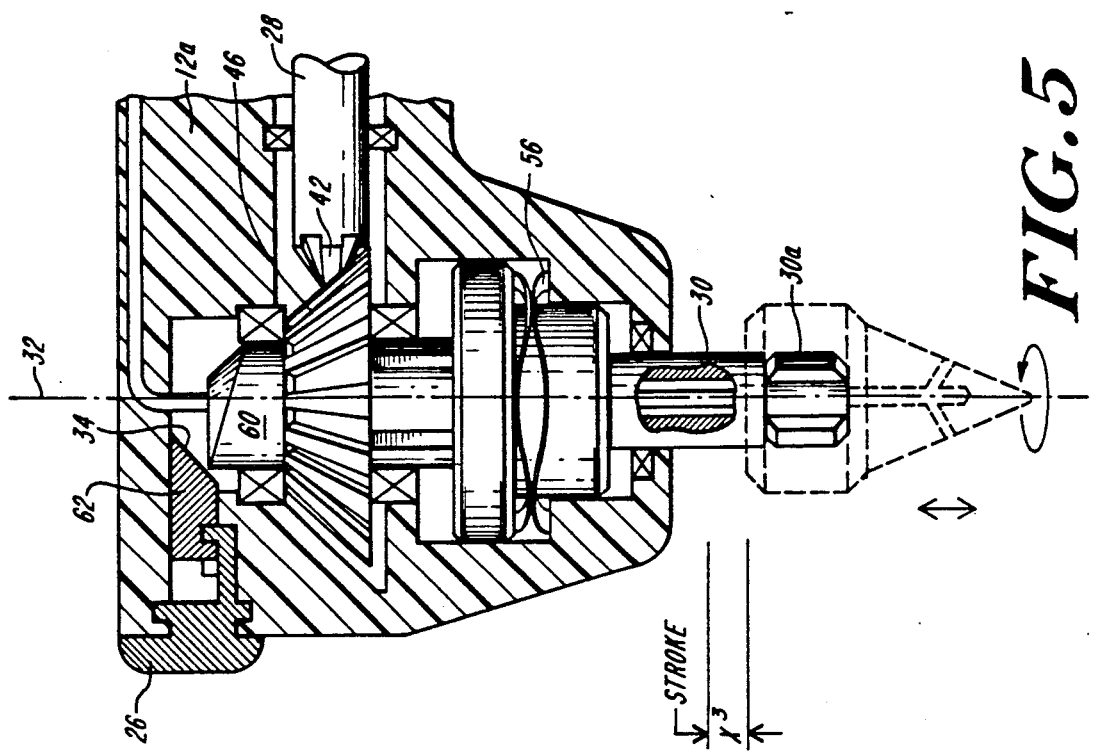
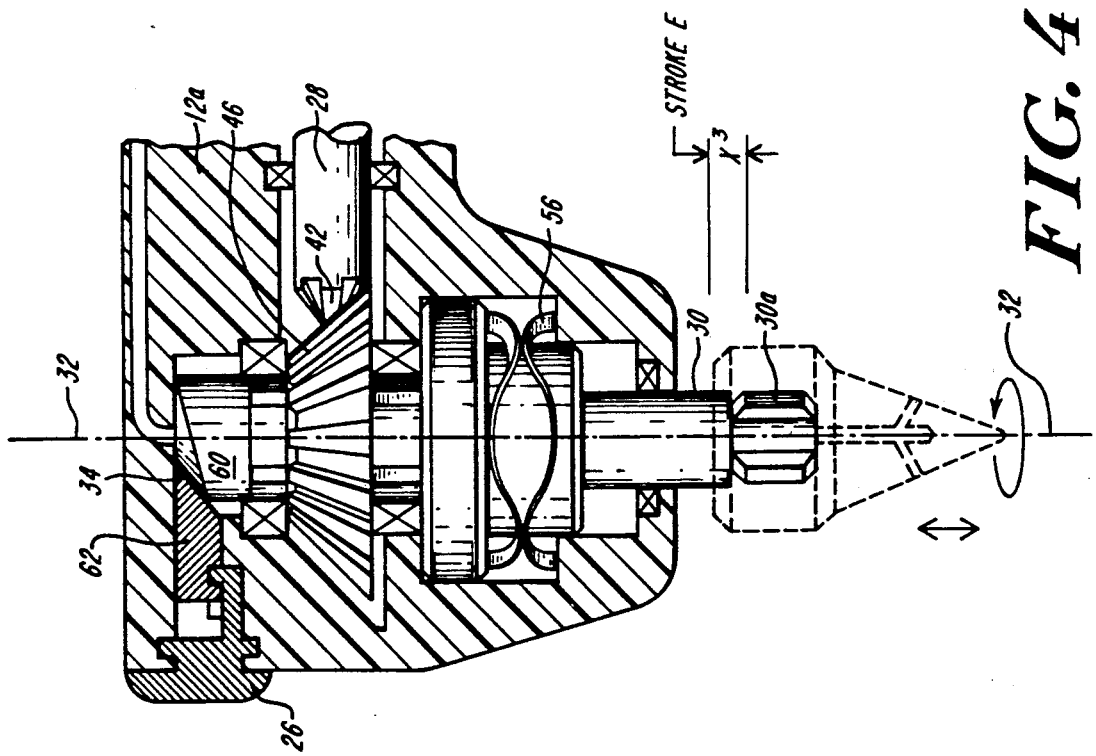

5,145,369

DENTAL TOOL DRIVING APPARATUS HAVING ROTATING AND ROTO-RECIPROCATING MOTIONS

BACKGROUND

This invention relates to manually deployable dental tool apparatus for driving a tool implement. More particularly, the invention provides such apparatus having both rotary and roto-reciprocating motions.

Prior dental tools combining rotary and axial motion include those disclosed in U.S. Pat. Nos. 4,175,324 (Arai); 4,629,426 (Levy); 4,341,519 (Kuhn et al.); 4,289,849 (Lustig et al.); and 4,544,356 (Gardella et al.). The prior devices of these patents are primarily for use by a dentist or other professional, and are not easily adaptable for home dental hygiene use. Further, the prior devices that provide both rotary and axial motion by means of eccentric cam rotation typically have a problem of radial wobble. This radial wobble is inconvenient for home users, and leads to imprecision during delicate procedures such as root canal therapy. It also can lead to excessive wear of internal parts. Additional problems of prior dental tools that provide combined rotary and axial motions include costly manufacture and mechanical complexity. They also have limited ability to discharge medication or other fluid during use.

Accordingly, it is an object of this invention to provide an improved manually deployable dental tool for driving a tool implement selectively with rotation and with rotary reciprocating axial motion.

Another object is to provide a dental tool of the above character having a stroke length that is variable and that can easily be adjusted. Moreover, it is an object to provide a dental tool of the above character that can readily be arranged to dispense fluid material to the dental site during operation.

A further object is to provide a dental tool of the above character having minimal radial wobble, and otherwise operating with minimal vibration.

It is also an object to provide a dental tool of the above character suitable for professional office or home hygiene use.

Other objects of the invention will in part be obvious and will in part appear hereinafter.

SUMMARY OF THE INVENTION

A tool according to the invention drives a tool implement with either of two motions. One is a rotating motion about an output axis, and a second is a roto-reciprocating motion of adjustable stroke length. The stroke length can be adjusted readily during operation.

The device has a hand-held housing that mounts an output shaft element for rotation about an output shaft and for reciprocation along the output axis. The output shaft has opposed first and second ends, and the first end is arranged for removably and replaceably mounting a tool implement. An input element is mounted with the housing for driven rotation about an input axis extending transversely relative to the output axis. An intermediate element couples the driving rotation of the input element to rotate the output shaft. This coupling element can be a gear engaged with gear teeth on the input element and keyed to the output shaft element, so that the output element is free for axial reciprocation during rotation.

Because of the free axial movement between the gear and the output shaft element, a cam mechanism at the second end of the output shaft element, combined with a spring, can impart rotary axial reciprocation to the output element as it rotates. The cam mechanism is adjustable to vary the stroke length of the reciprocation.

More particularly, a tool according to the invention features improvements in axial reciprocating movement of the output shaft and correspondingly the mounted tool implement. The output shaft is drivingly engaged at the second end with a cam. Rotational movement of the cam, specifically a cam surface that extends circumferentially about the output axis, relative to a cam follower imparts axial movement to the output shaft in a thrusting, outward direction to define the reciprocal stroke length. With this combined rotation and reciprocation, a point on the tool output shaft travels through an eliptical path with each full rotation of the shaft. Changing the stroke length of the reciprocation changes the length of one axis of this eliptical trajectory.

A preferred cam follower is mounted with the housing and has a ramp-shaped cam engaging surface for selective adjustable engagement with the cam, to adjust the length of the reciprocation stroke.

A further feature of the invention is a stroke adjusting element movably engaged with the housing. The stroke adjusting element, in one embodiment, eccentrically rotates about the cam, to enable the cam follower to selectively engage the cam. The cam follower preferably is adjustably movable between a first, fully engaged, position, where it is fully engaged with the cam to impart maximal axial movement to the output shaft; and a second, disengaged, position distal to the first position. When the cam follower is in the disengaged position, the output shaft rotates without reciprocation. At intermediate positions of the cam follower, the output shaft rotates with reciprocation of selected stroke length. The stroke adjusting element preferably is manually accessible by the user for continuous and gradual stroke length adjustment during operation.

Another feature of the invention is a spring mechanism resiliently engaged between the housing and the output shaft. The spring mechanism imparts a resilient restoring force in the direction opposite the reciprocation force imposed by the cam. Thus, the outward reciprocation stroke exerted on the output shaft by the cam and cam follower arrangement is counteracted by an inward restoring force exerted by the spring mechanism, to impart reciprocal axial movement of the output shaft during rotation. In a preferred embodiment, the spring mechanism is a wave spring.

Further, a preferred embodiment of the ramp-shaped cam engaging surface is downwardly angled at forty-five degrees relative to the output axis.

The cam, which rotates about an axis, has a cam surface that extends, in the radial direction, traversely from that axis with different transverse angles at different circumferential positions. The cam surface thus has progressively different bevels, relative to a plane perpendicular to the axis about which it rotates, at progressively different circumferential positions. In a simple embodiment, the cam surface at one circumferential position extends radially at essentially ninety degrees transverse angle and hence has no, or minimal, bevel. At the diametrically opposite circumferential position, the cam surface has maximal bevel. The bevel of the cam surface has a continuous progressive transition between these two extreme bevels at circumferentially intermediate positions.

With this camming structure, the cam mechanism imparts cyclic outward motion to the output shaft, as that shaft and the cam rotate. Unlike prior devices, a cam according to the invention is concentrically drivingly engaged with the output shaft, and its surface is contoured to impart progressive outward axial motion to the output shaft, due to engagement with the cam follower.

The cam interfits with and can be mechanically fixed to the output shaft. A preferred construction employs a central protrusion on the cam seated in a central aperture in the output shaft. The cam and output shaft have reciprocating spline elements which interfit during assembly. The cam can be mechanically fixed to the output shaft, after assembly of the coupling device with the output shaft, by conventional means including an epoxy adhesive and heat or chemical bonding.

Other features of a tool according to the invention include a housing-carried reservoir for dispensing fluid material to the dental or other site being worked. The housing and the output shaft can have connecting passages for conveying fluid material from the reservoir through the housing, and along the passage in the output shaft, to be expelled either at the first end of the output shaft or from the tool implement attached thereto.

Although described with specific reference to a dentist tool, features of the invention may have application to other tools and to other cam mechanisms.

BRIEF DESCRIPTION OF THE DRAWINGS

FIGS. 4 and 5 are elevation views of the dental tool power head, similar to FIG. 2, with a different tool implement and with the cam follower engaged to produce roto-reciprocation of the tool, and further showing different reciprocation positions of the output shaft;

DESCRIPTION OF ILLUSTRATED EMBODIMENTS

Figure 1:
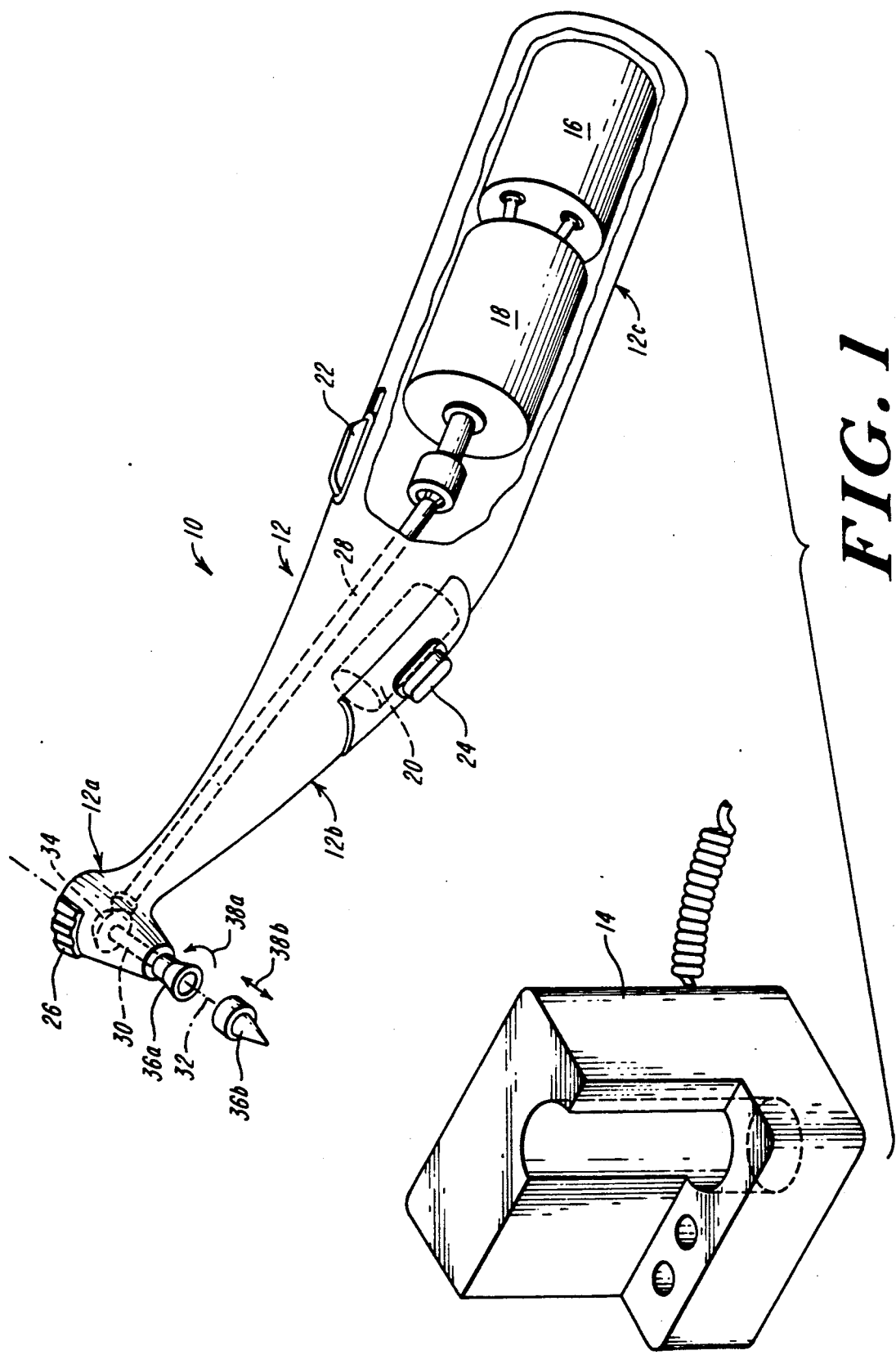
FIG. 1 is a perspective view, partly broken away, of a dental tool embodying the invention and a battery-charging base for the dental tool.

FIG. 1 shows a dental tool 10 according to the invention and having a manually deployable housing 12. The tool can be seated in a power charging base 14 for recharging a rechargeable battery 16 carried in the housing. The housing has an axial succession of three sections, namely a forward power head or tool section 12a, a central handle section 12b, and a back section 12c illustrated as housing the rechargeable battery 16 that drives an electric motor 18. The housing back section 12c also mounts a reservoir 20 of liquid, such as medication for selective dispensing to the dental site being treated with the tool. Also mounted on the tool housing 12 are an on/off switch 22 and a fluid dispensing control switch 24.

The tool housing is sized for an operator to hold it with fingers encircled around it and with the thumb or forefinger able to reach and operate the on/off switch 22, the fluid dispensing switch 24, and a stroke-adjusting switch 26 located on the forward power head section 12a.

When the power switch 22 is turned on, the battery-driven motor 18 rotates an input shaft 28 that is mounted within the housing 12. The driven rotation of the input shaft 28 is coupled to an output shaft 30 for rotating it about an output axis 32. In the illustrated tool, the output shaft extends along an axis 32 extending transversely to the axis of the shaft 28. A cam mechanism 34, mounted in the tool power head section 12a and coupled with the output shaft 30 and with the stroke adjusting switch 26, imparts reciprocation to the tool output shaft 30 during this driven rotation. The length of the reciprocation stroke is adjustable by movement of the stroke switch 26.

As also shown in FIG. 1, the tool output shaft 30 can snap fit with any of several different tool implements 36a and 36b. The illustrated tool implement 36a is operated with rotation only, about the tool output shaft 30, as designated with arrow 38a. The tool implement 36b is preferably employed with combined rotation and axially reciprocation, as designated with arrows 38b. Thus, one feature of the tool 10 is to drive interchangeable elements with exclusively rotary motion or with combined rotary and reciprocating motion.

Figure 2:
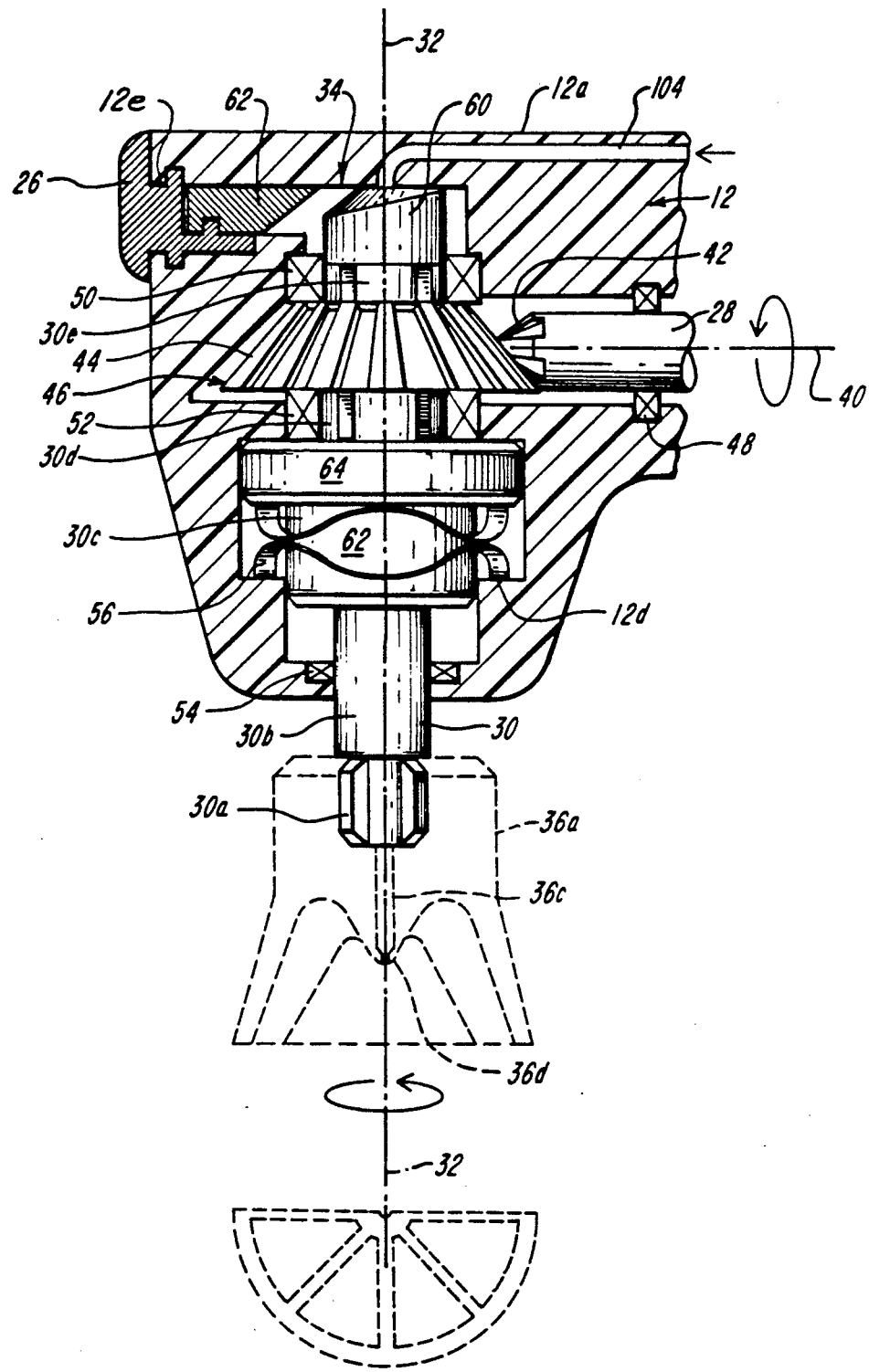
FIG. 2 is a side elevation view, partly cut away, of the power head portion of the dental tool of FIG. 1, with a tool implement mounted thereon and with the cam follower disengaged to produce only rotation of the tool.
Figure 3:
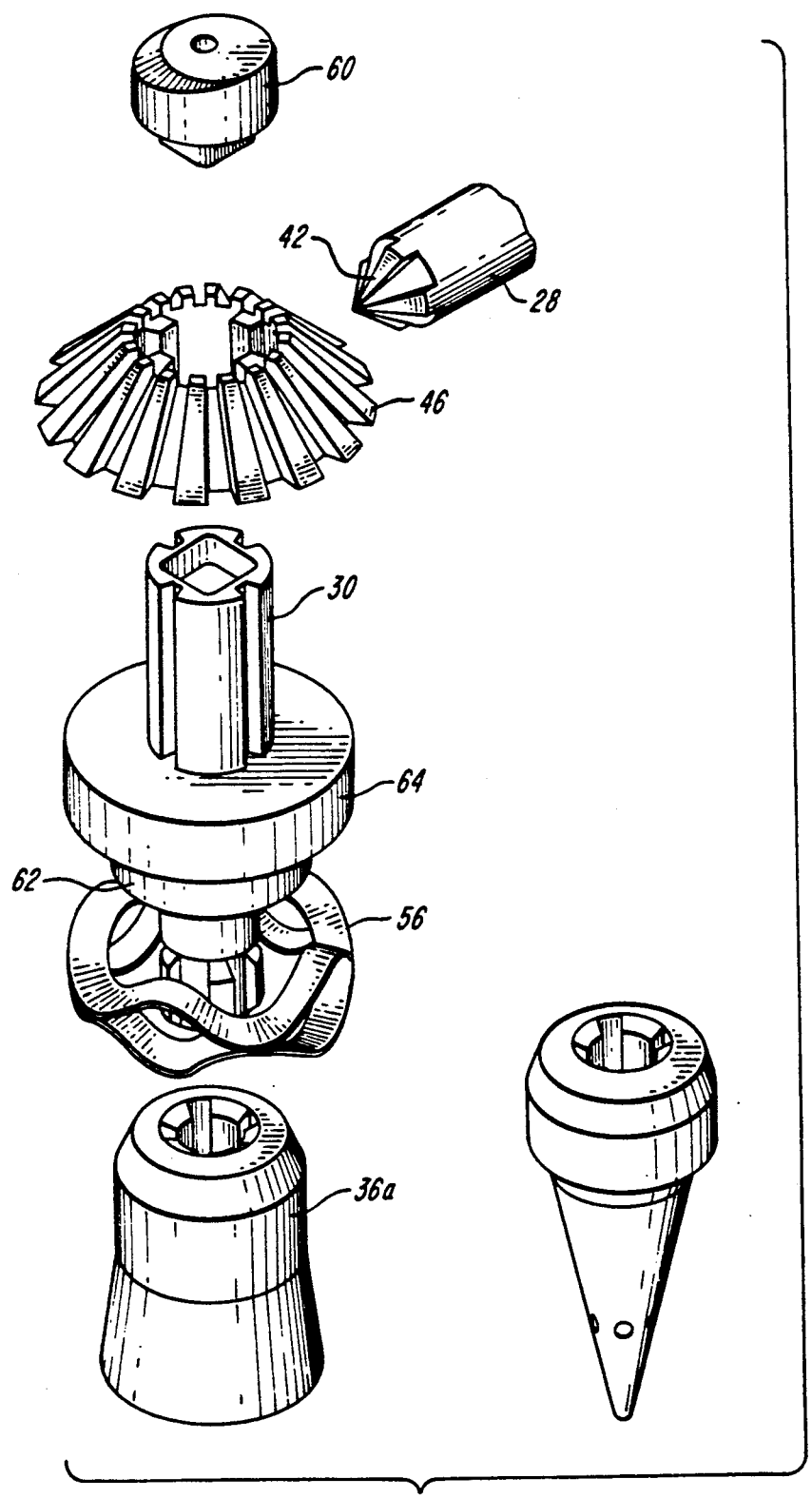
FIG. 3 is an exploded view of drive elements of the power head of the dental tool of FIG. 1.

With reference to FIGS. 2 and 3, the illustrated tool housing 12 mounts the input shaft 28 for rotation about an axis 40 longitudinal with the axial arrangement of the housing sections 12a, 12b, and 12c. The illustrated input shaft 28 has, at its forward output end in the housing power section 12a, a bevel gear 42 that is drivingly engaged with a mating bevel gear 44 on a gear element 46. The output, gear end of the input shaft 28 is mounted relative to the housing 12 for rotation about the axis 40 by way of a bearing 48. A pair of bearings 50 and 52 seated with the housing rotatably mount the gear element 46 for rotation about the output axis 32 and in fixed position axially along that axis for maintaining engagement between the bevel gears 42 and 44.

The gear element 46 is seated on the output shaft 30 and keyed with it, by internally projecting keys on the gear that slideably seat in axial key slots on the shaft 30, to rotate the output shaft in response to driven rotation which the gear element 46 receives from the input shaft 28. The keyed engagement of the gear element 46 with the output shaft 30 allows the output shaft to reciprocate along the output axis 32 independent of the gear element 46.

With further reference to FIGS. 2 and 3, the illustrated output shaft 30 has, in succession along the axis 32, a tool mounting end 30a, a bearing shaft section 30b that slideably seats within a bearing 54, a thrust section 30c engaged with a restoring spring 56, a key or spline section 30d fitted within the gear element 46, and a spline end section 30e illustrated as engaged with a thrust cam 60 that is part of the cam mechanism 34.

The output shaft 30 is thus mounted relative to the housing 12, by way of the bearing 54 and indirectly by way of the bearings 50 and 52 that engage the gear element 46 with which the shaft is engaged at the spline section 30d, for rotation about the output axis 30 and for limited axial reciprocation.

The output shaft thrust section 30c in the illustrated embodiment has a cylindrical collar 62 of enlarged radius for centering the restoring spring 56, and has a cylindrical flange 64 of larger radius for compressive abutment against the restoring spring 56. The illustrated restoring spring 56 is a compressive spring of annular configuration seated around the shaft collar 62 and compressed between the axial face of the shaft flange 64 and an axially opposing annular shoulder 12d of the housing 12. The spring 56, which preferably as illustrated is a compound wave spring, exerts a resilient reciprocation-restoring thrust on the output shaft 30 directed inward along the output axis 32, i.e. directed away from the shaft tool end 30a and upward in FIG. 2.

The output shaft key section 30d mountingly interfits within the gear element 46 for rotation with the gear element about the axis 32 and for movement along that axis independent of the gear element. The output shaft spline section 30e has a splined tubular inner passage into which a mounting stem of the cam 60 telescopically fittingly assembles. The illustrated splined passage has a square cross section and the cam stem has a correspondingly square peg-like axially extending shape for secure fit within the spline section.

The assemblage of the output shaft 30 and gear element 46 and cam 60 is thus mounted in the tool head section 12a with the spring 56 resiliently urging the output shaft upward in FIG. 1 and with the shaft free for rotation, and free for axial reciprocation against the urging of the spring 56. With this construction, rotation of the input shaft 28 about the longitudinal axis 40 is transferred by the bevel gear 42 to the mating bevel gear 44 of the gear element 46, which in turn rotates the output shaft 30.

FIG. 2 shows a cam follower 62 of the cam mechanism 34 adjustably positioned out of engagement with the cam 60. In this position, the dental tool 10 output shaft 30 rotates without any axial reciprocation.

Upon movement of the stroke adjusting switch 26 to engage the cam follower 62 with the cam 60, the tool output shaft 30 reciprocates along the output axis during rotation, as now described with reference to FIGS. 4, 5, and 7.

To obtain axial reciprocation of the output shaft 30, the cam mechanism 34 deflects the output shaft 30 to move the tool end 30a outward from the housing 12, i.e. downward in FIGS. 4 and 5 with each rotation of the shaft. The restoring spring drives the shaft back into the housing, i.e. upward in FIG. 2 to complete the reciprocating stroke. The illustrated cam mechanism employs the cam 60 rotatable on the inner end of the shaft 30 and a cam follower 62 that selectively interferes with the cam 60, forcing it to deflect along the output axis 32, during each shaft rotation.

The illustrated cam 60, as shown in FIG. 3 and in the series of views of FIG. 7, is a cylindrical member extending axially from the shaft 30, and selectively domed with a cam surface 60a, on the outer axial end. The cam surface engages the illustrated cam follower 62 at a fixed radial position.

The cam surface 60a generally extends transversely to the axis 32 about which it rotates and with progressively different circumferential positions thereon having progressively different bevels relative to a plane perpendicular the axis 32. The cam surface thus faces axially, i.e. along the axis 32. The bevels can have different contours, including flat, as in the embodiment of FIG. 7, and rounded as in the embodiment of FIG. 3 and with a different radius at different circumferential positions.

Figure 7A:
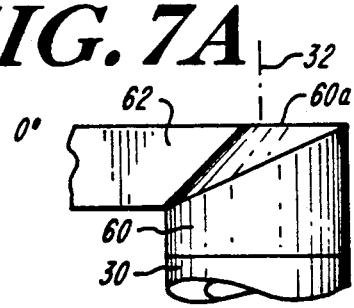
FIGS. 7A, 7B, 7C, and 7D illustrate the axial rotary reciprocation at different rotational positions of the output shaft of the tool of FIG. 1.

FIG. 7A shows the cam 60 in a first rotational position, designated 0°, where the cam surface 60a presents a maximal bevel to the cam follower 62. At this rotational position of the cam 60, it is free of interfering engagement with the cam follower, with the follower adjusted to the position shown. Accordingly, there is no axial deflection of the cam, and correspondingly of the output shaft 30. The restoring spring 56 hence maintains the output shaft 30 at a fully retracted position.

Figure 7B:
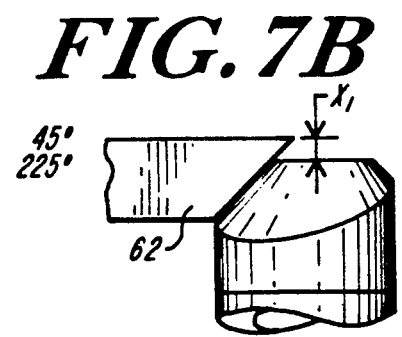

The bevel of the cam surface 60a that engages the cam follower 62 diminishes as the cam rotates from the 0° position. FIG. 7B shows that at a 45° rotational position of the cam, and symmetrically at a 225° rotation of the cam, the cam surface interferingly engages with the cam follower 62 to deflect the cam and correspondingly the output shaft by a stroke distance designated ($x_1$).

Figure 7C:
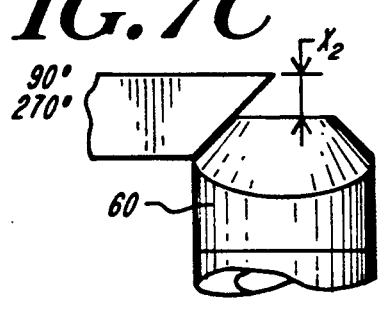

The progressively changing bevel of the cam surface 60a engaged with the cam follower 62 diminishes further as the cam rotates, so that at 90° and 270° rotations of the cam 60, as shown in FIG. 7C, there is increased interference between the cam 60 with the cam follower to produce a larger reciprocating displacement, designated ($x_2$).

Figure 7D:
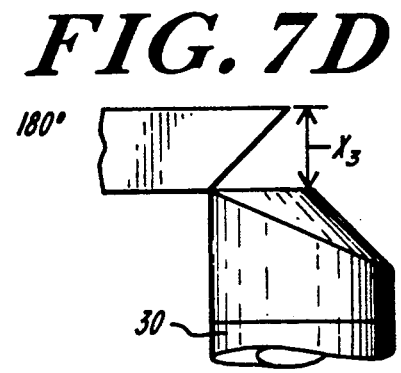

FIG. 7D shows that the 180° rotational position of the cam 60, the cam surface presents a minimal deflection to the cam follower 62 and there accordingly is maximal reciprocating displacement, designated ($x_3$) of the cam and correspondingly of the output shaft 30.

FIG. 4 shows the tool 10 power head at the minimal reciprocating displacement of the output shaft 30, corresponding to the 0° rotational position of the cam 60 as shown in FIG. 7A. FIG. 5 shows the tool power head with maximal reciprocating displacement of the output shaft, corresponding to the 180° rotational position of the cam 60 as shown in FIG. 7D. The cam follower 62 has the same position in each of FIGS. 4 and 5. FIG. 5 shows the increased compression of the restoring spring 56, with increased displacement of the output shaft.

Figure 8:
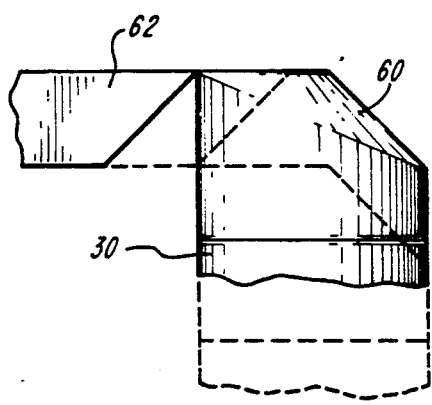
FIG. 8 is a diagrammatic showing of different positions of the cam follower of the tool of FIG. 1 and corresponding different reciprocation positions of the tool output shaft.

FIG. 8 illustrates the adjustment of the reciprocating stroke length due to adjustable positioning of the cam follower 62. The cam follower position as shown with solid lines presents minimal interference with the cam 60, in the illustrated instance no interference. Consequently, there is no reciprocation of the output shaft, as indicated with the solid line showing of the cam 60 and of the shaft 30 in FIG. 8.

When the cam follower is adjustably positioned for maximal interference, as shown in FIG. 8 with dash lines, it produces a maximal output shaft deflection, as illustrated with the dotted showing of the cam 60 and of the output shaft. At intermediate positions of the cam follower, the output shaft reciprocation has intermediate stroke lengths.

Figure 9A:
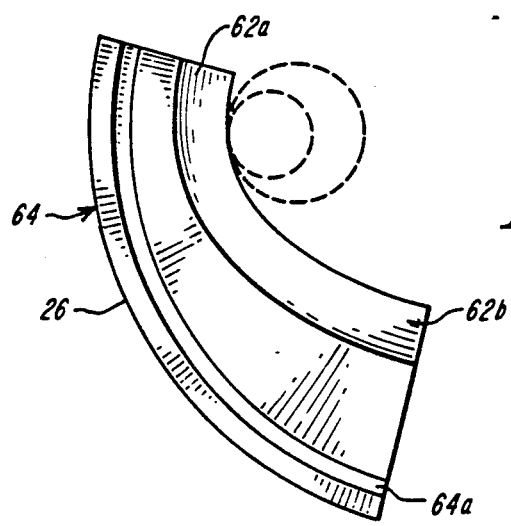
FIGS. 9A and 9B are fragmentary plan and elevation views respectively of one stroke adjusting mechanism for use with the tool of FIG. 1.
Figure 10A:
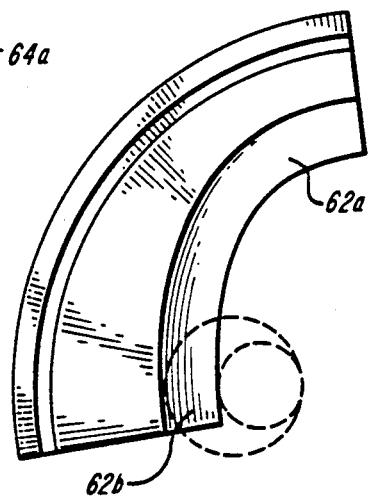
FIGS. 10A and 10B are fragmentary and side elevation views of a second stroke adjusting mechanism for the tool of FIG. 1.

The stroke adjusting switch 26 of the embodiment of the tool 10 shown FIG. 1 is integral with the cam follower 62, as FIGS. 9 and 10 show. A one-piece adjustment member 64 forms both the switch 26 and the cam follower 62. More particularly, the switch 26 is a protrusion on the member 64 outward from the housing 12, through a slot 12e (FIG. 2), for manual access by a user. The switch 26, and a of the member 64 which carries the switch and seats in the housing slot 12e, are elongated along concentric circular paths, as shown in the plan views of FIGS. 9A and 10A. The housing slot 12e follows a circular path that matches the path of the web 64a which the slot seats.

The cam follower 62 is a beveled, concentrically inner extension of the adjustment member 64 and is radially located inward from the web 64a and is elongated along a non-circular path of progressively decreasing radius from one end 62a to the other end 62b.

Figure 9B:
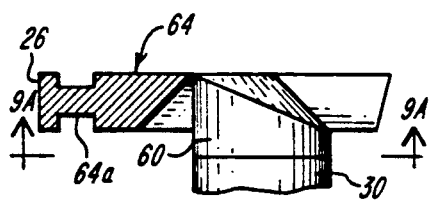
Figure 10B:
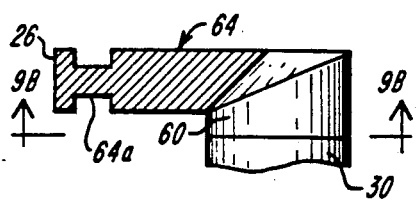

With this construction, when the illustrated adjustment member 64 is slideably moved to the extreme counterclockwise position shown in FIGS. 9A and 9B, the cam follower end 62a is positioned adjacent the cam 60. This is the position of minimum interference of the cam follower with the cam, as FIG. 9B shows, and accordingly produces zero or selected minimal reciprocation of the output shaft 30 of the tool 10. Movement of the switch 26 counterclockwise from the position shown in FIG. 9A brings the cam follower increasingly into engagement with the cam 60, and accordingly produces progressively increasing reciprocation of the tool output shaft. FIGS. 10A and 10B show the position of maximal interference between the cam follower 62 and the cam 60, and correspondingly of maximal reciprocating stroke of the tool output shaft.

Figure 11B:
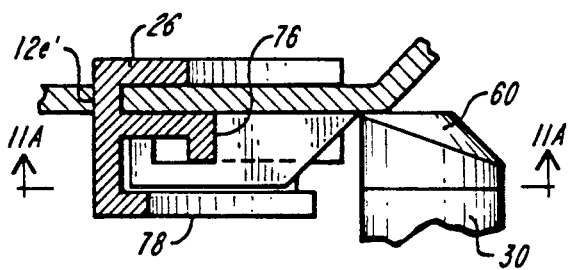
FIGS. 11A, 11B, 11C, and 11D show fragmentary plan and elevation views of a third stroke adjusting mechanism for use with the power tool of FIG. 1 in different rotational positions.
Figure 11D:
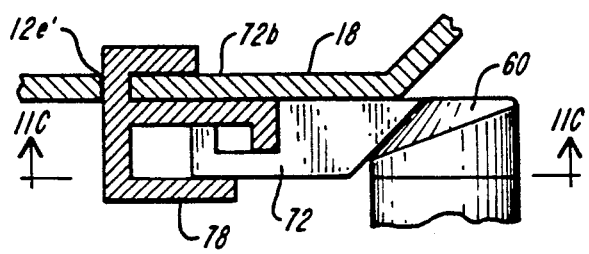

FIGS. 11A through 11D show a second embodiment that employs a stroke adjusting switch 70 linked to a separate cam follower 72. The switch 70 is on an adjustment member 74 that is slideable along a circular housing slot 12e, as in the embodiment of FIGS. 9 and 10. The switch 70 and correspondingly the housing slot 12e' of the embodiment of FIG. 11 are illustrated as being on a top side of the housing, in contrast to the lateral side location shown in FIGS. 9 and 10. The adjustment member 74 slidingly engages the cam follower 72 with an arcuate rim 76a of diminishing radius between circumferentially spaced ends 76a and 76b. The illustrated adjustment member 74 also has a shelf 78 axially spaced from the rim 76 for seating the cam follower 72 between the rim and the shelf, as FIGS. 11B and 11D show.

With further reference to FIGS. 11A through 11D, the cam follower 72 is a wedge-like member arranged to move in a direction radial to the axis 32, i.e. along the arrow 80. The cam follower can be seated in a slot within the housing or have a slot radial to the axis 32 that receives a housing rail, or incorporate similar structures apparent to those skilled in the art to confine the movement of the cam follower to this sliding radial path. The cam follower has a camming surface 72a at its radially innermost end and that conforms to the beveled camming surface on the cam 60. The radially outer end of the cam follower 72 has a slot 72b that slidingly interfits with and receives the rim 76, for radially positioning the cam follower.

Figure 11A:
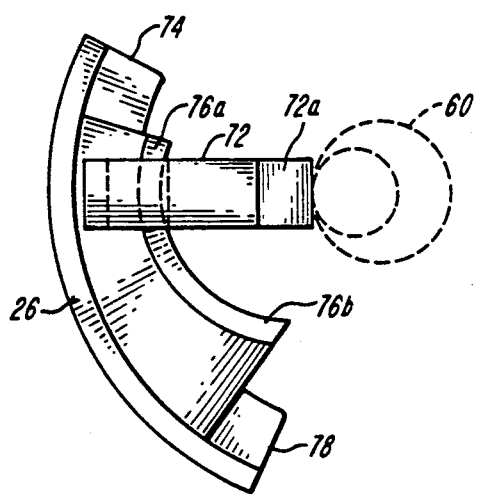
Figure 11C:
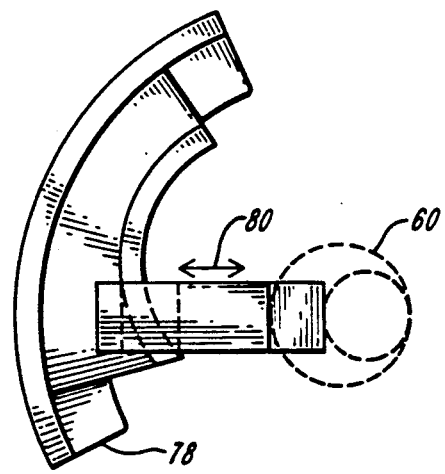

FIGS. 11A and 11B show that when the adjustment member 74 is in the extreme counterclockwise position, the section of the cam-positioning rim 76 engaged with the cam follower 72 has a large radial value. The cam follower 72 is accordingly positioned for minimal reciprocation of the tool output shaft. Movement of the adjustment member 74 clockwise from the position of FIGS. 11A and 11B increasingly moves the cam follower 72 radially inward toward the axis 32 and into increasing engagement with the cam 60, thereby producing increasing reciprocation of the tool output shaft. FIGS. 11C and 11D show the adjustment member 74 in its full clockwise rotational position, where it positions the cam follower 72 for maximal reciprocating stroke length.

Figure 12A:
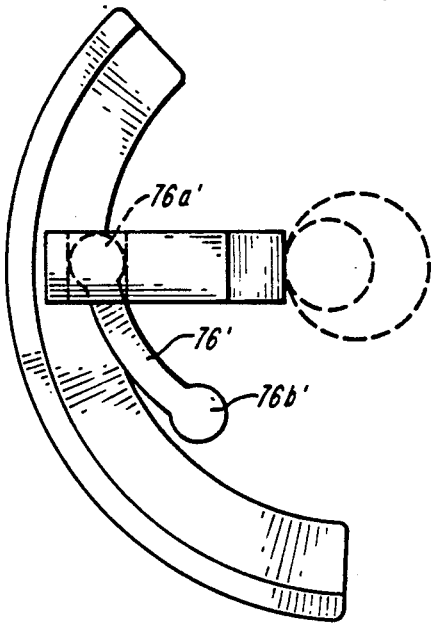
FIGS. 12A and 12B are fragmentary plan views of a modification of the stroke adjusting mechanism of FIGS. 11A—11D in different rotational positions.
Figure 12B:
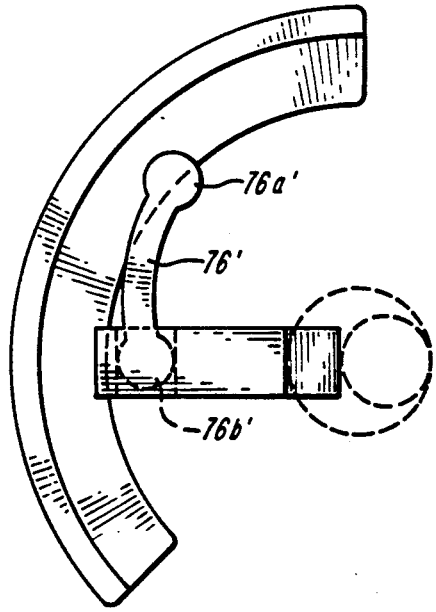

FIGS. 12A and 12B show a modification of the adjustment mechanism of FIG. 11 to provide a detent-like action at the travel limits of the adjustment member 74. The positioning rim 76' has bulbous enlargements at each circumferential end 76a' and 76b'.

Figure 13A:
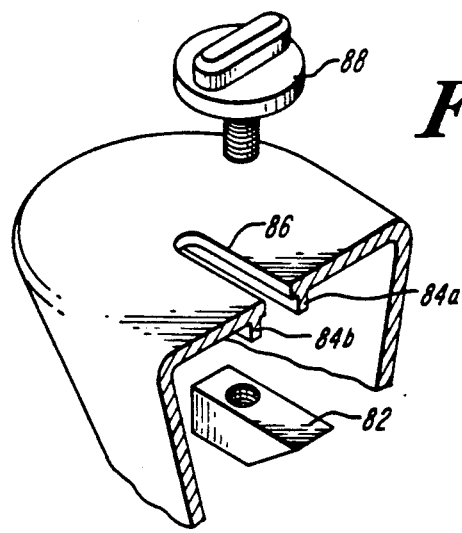
FIGS. 13A and 13B are fragmentary perspective and side elevation views respectively of another stroke adjusting mechanism embodying features of the invention.
Figure 13B:
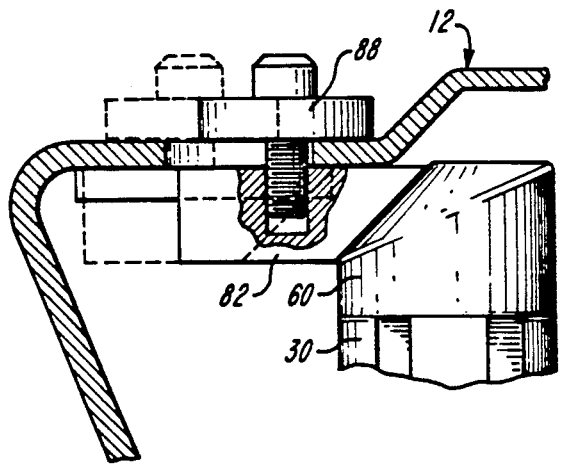

Another embodiment of the stroke adjusting mechanism for the tool 10, shown in FIGS. 13A and 13B, employs a wedge-like cam follower 82 slidably seated within the housing between housing rails 84a and 84b that flank a housing slot 86. A thumb screw 88 is threaded to the top of the cam follower, through the housing slot 86. With this construction, adjustment of the tool reciprocation stroke simply involves loosening the thumb screw 88 and sliding it, with the cam follower 82, along the housing slot 86 and again tightening the thumb screw to secure the cam follower in the desired position radial to the output axis 32.

Figure 14A:
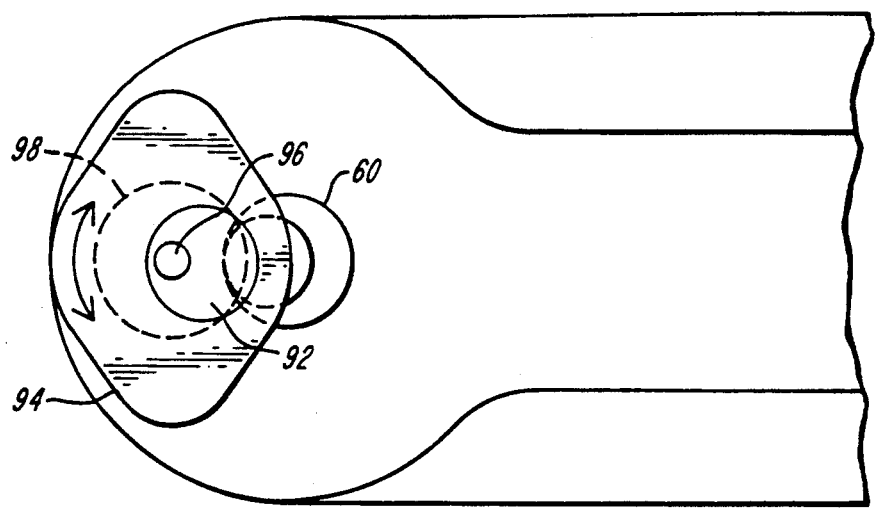
FIGS. 14A, 14B, and 14C are two plan views and one elevation view respectively of a further stroke adjusting mechanism for use with the power tool of FIG. 1 and embodying features of the invention.
Figure 14B:
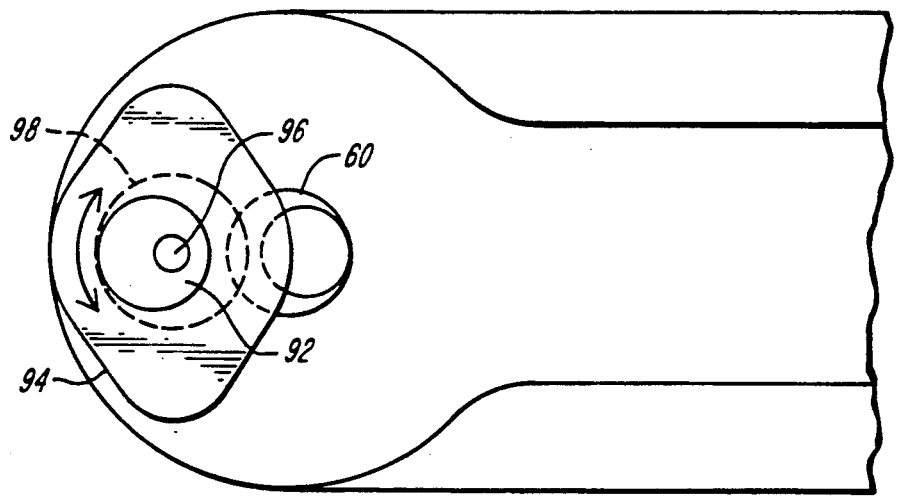
Figure 14C:
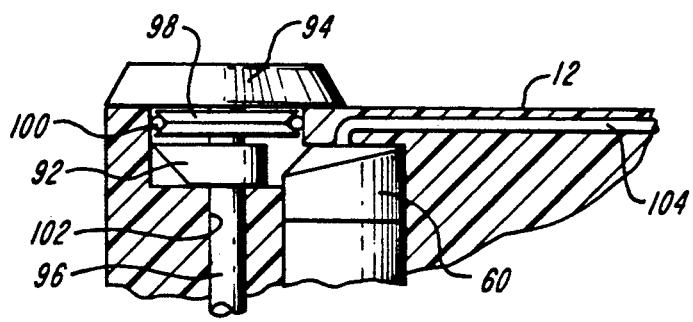

A further embodiment of a tool according to the invention has, as shown in FIG. 14, a cam 60 as previously described on the end of the tool shaft 30 and engaged by a rotary adjustable cam follower 92 to select the stroke length of output shaft reciprocation. More particularly, the tool of FIG. 14 has a rotary stroke adjusting switch 94 accessible on the top side of the tool housing. The rotary switch 94 is on a stem 96 that passes through a housing opening to mount a rotary cam follower 92 within the housing. A rotary sealing disk 98, illustrated as carrying an O-ring 100 that sealingly slidably engages the housing wall, is also mounted on the stem 96 to seal the housing opening from dirt, spillage and other debris. The stem 96, which extends parallel to the output shaft axis 32, extends axially within the housing beyond the cam follower 92 to seat in a support socket 102, typically recessing an inner projection of the housing.

The illustrated rotary cam follower 92 has a circular frusto-conical shape to engage the cam 60 with a beveled camming surface. The cam follower is mounted off-center to the stem 96, and hence rotates about an off-center axis.

With further reference to FIGS. 14A, B, and C, the rotary adjustment switch 94 and cam follower 92 are arranged to rotate as a unit with the stem 96, as well as with the sealing disk 98. Rotary adjustment of the switch 94 rotates the cam follower 92 from the position shown in FIG. 14B, where it has minimal interference with the cam 60, progressively through 180° to the position shown in FIG. 14A, where the cam follower has maximal interference with the shaft carried cam 60.

Figure 6:
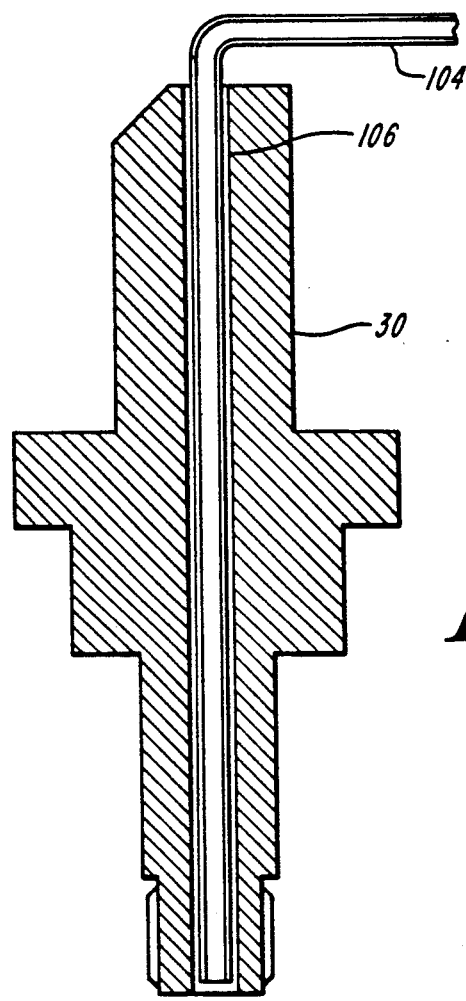
FIG. 6 is a side elevation showing of the liquid discharging conduit and passage for the dental tool of FIG. 1.

A further feature of the tool 10 is that it can dispense liquid, such as medication or a dental cleaning preparation, to the dental site being treated. The tool housing 12 carries a reservoir 20 and fluid dispensing switch 24, as shown in FIG. 1. A tube 104 feeds liquid from the reservoir 20 to the forward power head section of the housing and, as shown in FIGS. 2 and 6, through a central bore 106 in the cam 60 and in output shaft 30. The illustrated tube 104 extends substantially the full length of the output shaft to discharge liquid directly into whatever tool implement is fitted on the output shaft. The tool implement 36a, shown in FIGS. 1 and 2, has a central passage 36c for receiving liquid discharged from the tube 104, and delivering it to the dental site. The passage of the tool implement 36a preferably ends with an orifice 36d that is normally closed and that opens in response to the implement being pressed onto a surface. Thus, the operator of the tool 10 fitted with the implement 36a can control the discharge of liquid both with the switch 24 on the tool housing and, further, by controlling the pressure with which the tool implement is pushed onto the dental site being treated.

FIGS. 4 and 5 show that the tool implement 36b also has a central passage for receiving liquid from the tube 104 and that feeds into radial discharge ducts from which the liquid is dispensed to the dental site being treated.

A tool having the features described hereinabove thus rotates an output shaft and provides axial reciprocation of the shaft, with adjustable reciprocation stroke with a mechanism that operates with minimal vibration and without eccentric wobble-producing elements. The drive mechanism of the tool has a high degree of axial symmetry that enhances smooth operation and enhances the ready delivery of liquid medication and like substances to the site being treated. The tool can employ a number of different adjustment mechanisms for controlling the stroke of the axial reciprocation.

It will thus be seen that the objects set forth above, among those made apparent from the preceding description, are efficiently attained. Since certain changes may be made in the above constructions without departing from the scope of the invention, it is intended that all matter contained in the above description or shown in the accompanying drawings be interpreted as illustrative and not in a limiting sense. It is also to be understood that the following claims are to cover all of the generic and specific features of the invention herein described and all statements of the scope of the invention which, as a matter of language, might be said to fall therebetween.

Having described the invention, what is claimed as new and secured by Letters Patent is:

1. Manually deployable tool apparatus for driving a tool implement with rotating motion about a first axis combined with axial reciprocation of adjustable stroke length, said apparatus comprising
A. means forming a manually deployable housing,
B. output shaft means mounted with said housing for rotation about and reciprocation along said first axis,
  (i) said output shaft means having opposed first and second ends,
  (ii) said first end being arranged for removably and replaceably mounting a tool implement,
C. input means mounted with said housing for driven rotation and engaged with said output shaft means for rotating said output shaft means about said first axis,
D. cam means drivingly engaged with said output shaft means for imparting to said output shaft means axial movement in a first direction during driven rotation of said output shaft, and
E. cam follower means mounted with said housing and including a cam engaging surface for selective adjustable engagement with said cam means for moving said cam means to impart said axial movement and to adjust said stroke length.

2. Apparatus according to claim 1 wherein said cam means has a camming surface extending circumferentially about said first axis, said camming surface having sequentially different bevels, relative to a plane transverse to said first axis, at sequentially different circumferential locations.

3. Apparatus according to claim 1 wherein said cam means is mounted for rotation concentrically with said output shaft means.

4. Apparatus according to claim 1 wherein said cam engaging surface is inclined at forty-five degrees relative to said first axis.

5. Apparatus according to claim 1 wherein said cam means is mechanically fixed to said second end of said output shaft for rotation and reciprocation therewith.

6. Apparatus according to claim 1 wherein
A. said cam means includes a first spline element extending longitudinal with said first axis, and
B. said output shaft means has a second spline element for matingly interfitting with said first spline element, for securing said cam means for rotation with said output shaft means.

7. Apparatus according to claim 1 further comprising stroke adjusting means movably mounted with said housing and manually accessible thereon for adjustably positioning said cam follower means relative to said cam means.

8. Apparatus according to claim 7 wherein said cam follower means has a first engaged position wherein said cam follower means is engaged with said cam means to impart said axial movement, and a second disengaged position distal to said first position wherein said output shaft means rotates about said first axis without said axial movement.

9. Apparatus according to claim 7 wherein said stroke adjusting means is slidably engaged with said housing for rotation about said cam means.

10. Apparatus according to claim 9 further comprising a cam follower housing element integral with said stroke adjusting means and slidably engaging said cam follower.

11. Apparatus according to claim 1 wherein said cam means is rotatable with said output shaft means about said first axis.

12. Apparatus according to claim 1 further comprising spring means resiliently engaged between said housing and said output shaft means for imparting axial movement to said output shaft means in a second direction opposite said first direction.

13. Apparatus according to claim 12 wherein said spring means includes a wave spring.

14. Apparatus according to claim 1 further comprising stroke adjusting means movably mounted with said housing and manually accessible thereon for adjustably positioning said cam follower means relative to said cam means, said adjusting means being movable substantially in a plan transverse to said first axis for effecting said adjustable positioning of said cam follower means.

15. Apparatus according to claim 1 further comprising means forming a passage in said housing and in said output shaft means for conveying fluid material from within said housing for delivery to said first end of said output shaft means.

16. Apparatus according to claim 1 in which said input means includes
   A. drive means mounted for driven rotation about a second axis extending transversely relative to said first axis, and
   B. coupling means engaged with said drive means and with said output shaft means for transferring rotation of said input means to rotation of said output shaft means.

17. Apparatus according to claim 16 wherein said coupling means includes gear means engaged with said output shaft means for rotation therewith and movable relative thereto along said first axis.

18. Apparatus according to claim 17 wherein said gear means comprises a bevel gear.

19. Cam apparatus for imparting movement along a first axis, said apparatus comprising
   A. cam follower means for acting radially relative to said axis,
   B. cam means rotatable about said first axis relative to said follower means and having a camming surface for sliding engagement with said follower means, said camming surface having progressively different bevels, relative to a plane transverse to said first axis, at progressively different radial positions, and
   C. means mounting said cam means relative to said follower means for rotation about said first axis and for camming displacement along said first axis, so that engagement of said camming surface with said follower means deflects said cam means along said first axis by different offsets as said cam means rotates.

20. Cam apparatus according to claim 19 further comprising resiliently acting restoring means supported relative to said mounting means, for resiliently displacing said cam means along said first axis opposite to the direction of said camming displacement.

21. Cam apparatus according to claim 19 further comprising means for adjustably positioning said follower means relative to said cam means, for selectively adjusting the engagement between said follower means and said cam means, thereby for selectively adjusting the stroke length of said camming displacement.

22. Cam apparatus according to claim 19 in which said camming surface is arranged for facing axially and has a minimal bevel at one circumferential location thereon and has a maximal bevel at a second circumferential location thereon located diametrically opposite first circumferential location.

23. Cam apparatus according to claim 19 in which said camming surface has rounded bevels, with the radius of the rounded bevel changing with circumferential position.

24. A method for driving a shaft with rotation about an axis concurrent with and axial oscillation of varying stroke-length, said method comprising the steps of
   A. rotating a shaft about the shaft axis,
   B. providing a camming surface on one end of said shaft,
      (i) said camming surface having a circumference with a bevel edge disposed at a fixed angle relative to said shaft axis,
      (ii) said bevel edge being off-center from the center of said shaft, such that the intersection of construction lines is offset from the center of said shaft where such construction lines contact and not intersect said camming surface and are spaced circumferentially thereabout and that are oriented at a first angel relative to said shaft axis,
   C. abuttingly engaging said beveled edge of said camming surface with a cam engaging surface that does not rotate with said shaft, said cam engaging surface having a selected beveled edge, and
   D. resiliently biasing said shaft axially toward said cam engaging surface,
   E. so that engagement of said cam engaging surface with said camming surface axially deflects said shaft against said resilient bias, with the stroke length of said axial deflection being determined by the position of said cam engaging surface radially relative to said shaft axis.

25. The method according to claim 24 wherein said first angle is forty-five degrees.

* * * * *